United States Patent [19]

Barba

[11] 4,405,047

[45] Sep. 20, 1983

[54] UNIT PACKAGE FOR POULTRY VACCINATION

[75] Inventor: Robert L. Barba, Georgetown, Del.

[73] Assignee: Sterling Drug, Inc., New York, N.Y.

[21] Appl. No.: 285,318

[22] Filed: Jul. 22, 1981

[51] Int. Cl.$^3$ .................. B65D 83/00; A61B 17/20
[52] U.S. Cl. .................................... 206/570; 206/223; 206/438; 128/303.1; 604/87
[58] Field of Search ............... 206/364, 365, 570, 571, 206/223, 438; 128/253

[56] References Cited

U.S. PATENT DOCUMENTS

| | | | |
|---|---|---|---|
| 2,568,108 | 9/1951 | Barton | 206/364 |
| 3,851,649 | 12/1974 | Villari | 206/571 |
| 4,296,786 | 10/1981 | Brignola | 206/365 |

*Primary Examiner*—William T. Dixson, Jr.

[57] ABSTRACT

The invention provides a unit package for use in connection with a system for supplying liquid vaccine composition to an apparatus for substantially simultaneously debeaking and vaccinating poultry chicks. The package comprises a compartmentalized container the compartments of which contain (a) a plurality of liquid diluent supply bottles containing sterile diluent for rehydrating dehydrated vaccine, (b) a transfer spike assembly comprising a cover unit sealed with a tear-away cover and containing a transfer spike suitable for providing sterile flow means from a liquid diluent supply bottle to a bottle containing dehydrated vaccine and (c) a drip chamber-tubing-clamp assembly suitable for sterile transfer of liquid vaccine from a liquid supply bottle to the liquid injecting means of an apparatus for substantially simultaneously debeaking and vaccinating poultry chicks.

1 Claim, 7 Drawing Figures

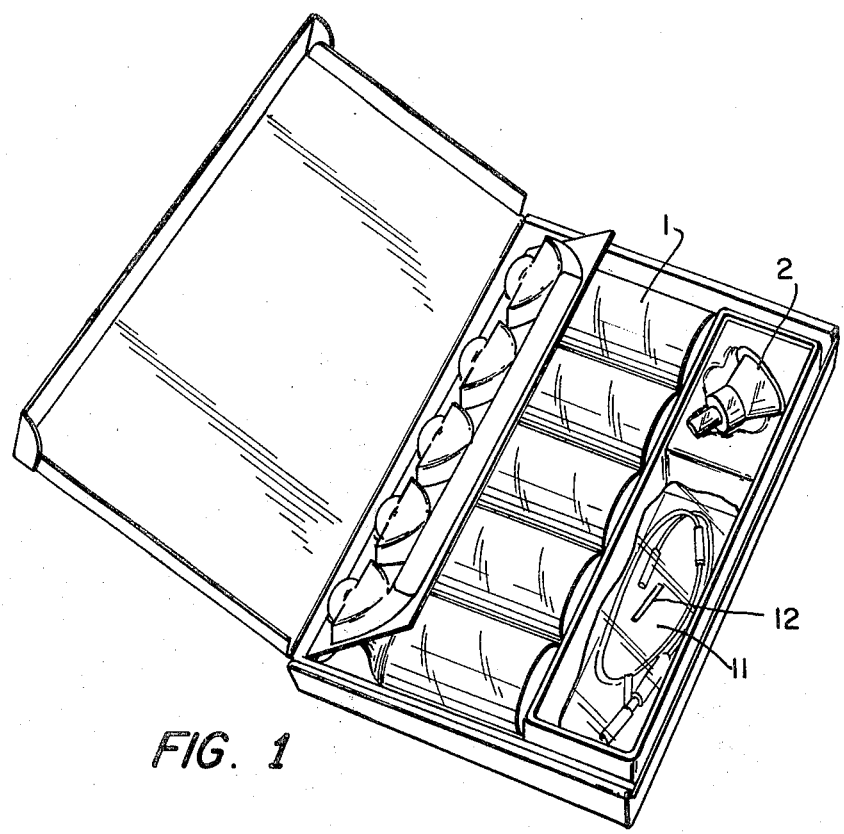
FIG. 1
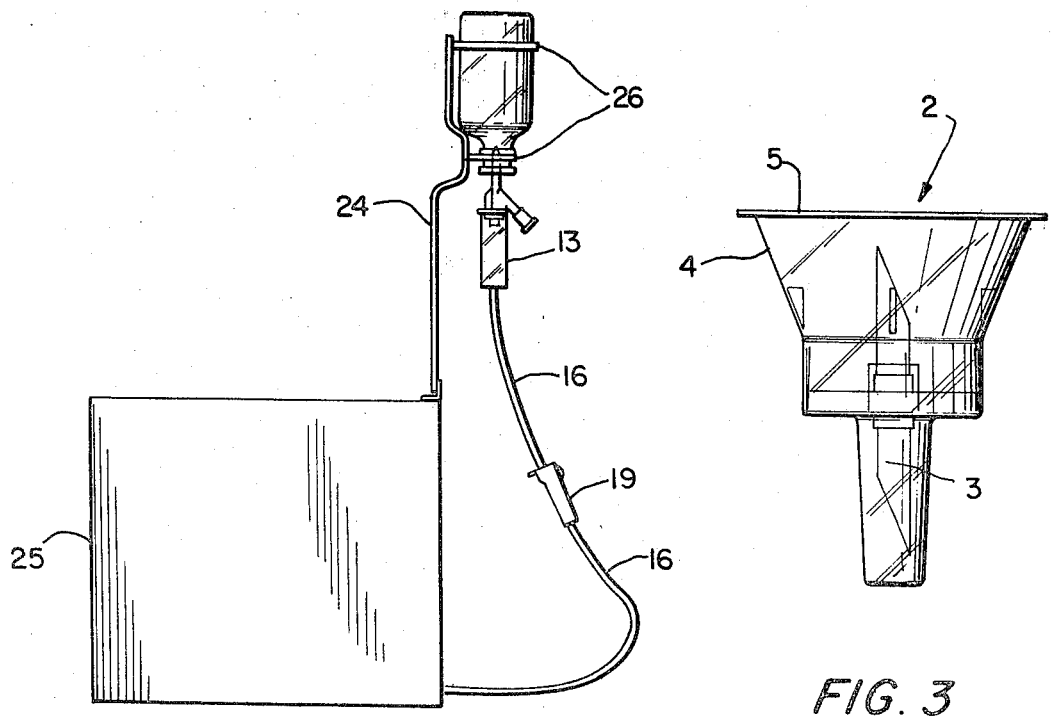
FIG. 2
FIG. 3

UNIT PACKAGE FOR POULTRY VACCINATION

BACKGROUND OF THE INVENTION

The present invention relates to the art of vaccinating and debeaking poultry such as baby chicks.

It is well known in the poultry industry that it is desirable to vaccinate baby fowl against disease and to simultaneously debeak or trim the upper half of the chick's beak as well as to count the chicks which have been treated. Vaccination ensures freedom from diseases such as pox, Newcastle disease and bronchitis. Debeaking reduces feather loss and other injuries caused by pecking of the chicks during processing and shipping.

Various methods of vaccination are known such as needle injection into the wing webbing or by dropping the vaccine into the eyes or nostrils of the bird.

As indicated, it is known to simultaneously debeak and vaccinate, and one particularly useful apparatus for doing so is the Beak-O-Vac, Inc. apparatus disclosed in U.S. Pat. No. 3,570,487. In such apparatus the chicks are vaccinated, debeaked and counted in a single operation. An operator grasps a chick in each hand, places a thumb at the base of the skull of each chick and a forefinger around the base of the lower beak of each chick and gently squeezes to open their beaks. The two halves of the beak of each chick are simultaneously placed about a pivotal beak support member, over apertures defined in the beak support member. The operator then thrusts the chicks forward, to pivot the beak support member toward a heated cauterizing element. Movement of the beak support member in this manner energizes a pump which is effective to inject vaccine through the apertures of the beak support member, into the oral cavity of each chick. The upper protruding half of the chick's beak engages the heated cauterizing element which is effective to sear and blunt the protruding beak. The beak support member is continuously cooled by circulating water so that the chick's tongue will not be burned during the operation. A counter is energized upon each depression of the beak support member so that the hatcheryman is able to determine the number of chicks treated and the effectiveness of the operator.

SUMMARY OF THE INVENTION

The present invention provides an improvement in apparatuses for simultaneously debeaking and vaccinating baby chicks, the improvement residing in providing a simple and efficient vaccine supply to the said apparatus. In general, the debeaking and vaccinating apparatus comprises a heated member for contacting and forming the chick's beak by searing the upper half of said beak, liquid injecting means for injecting liquid vaccine into the oral cavity of the chick's mouth substantially simultaneously with the searing of the beak and means for supplying the liquid vaccine to the said liquid injecting means. For a more detailed disclosure of such an apparatus, attention is directed to the previously referenced U.S. Pat. No. 3,570,487.

In accordance with the improvement of this invention, the liquid vaccine is supplied to the basic debeaking and vaccinating apparatus by a liquid vaccine supply apparatus which comprises a bracket which is adapted for attachment to the basic apparatus and which receives and holds in an inverted position a supply bottle containing the liquid vaccine composition. The liquid vaccine composition is supplied by gravity flow through a drip chamber-tubing-clamp assembly from the supply bottle to the debeaking and vaccinating apparatus.

The invention also provides a unit package which comprises sterile diluent supply bottles, transfer spike assembly and drip chamber-tubing-clamp assembly constituting a liquid vaccine supply system for use in association with the basic debeaking and vaccinating apparatus.

BRIEF DESCRIPTION OF THE DRAWINGS

FIG. 1 is a perspective view of the unit package of the invention.

FIG. 2 is a perspective view of the liquid vaccine supply system of the present invention.

FIG. 3 is a perspective view of the transfer spike assembly of the invention.

DETAILED DESCRIPTION OF THE INVENTION

Figure 6:
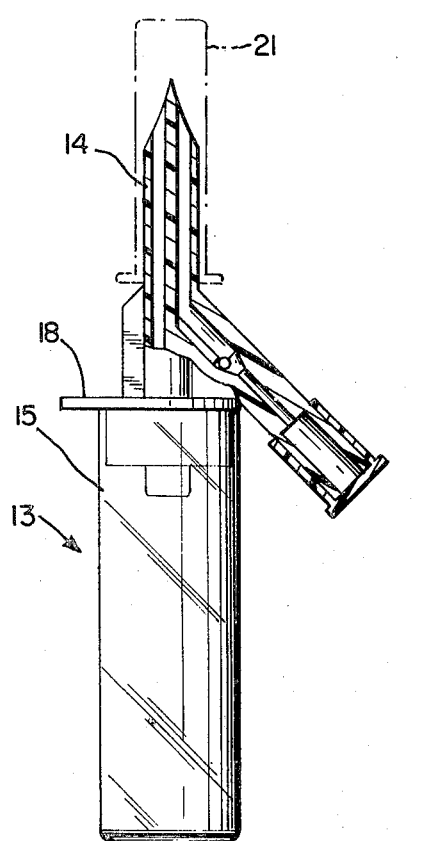
FIG. 6 is a partially sectional view of the drip chamber-tubing-clamp assembly of the invention.
Figure 6:
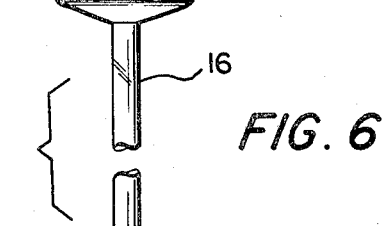
Figure 6:
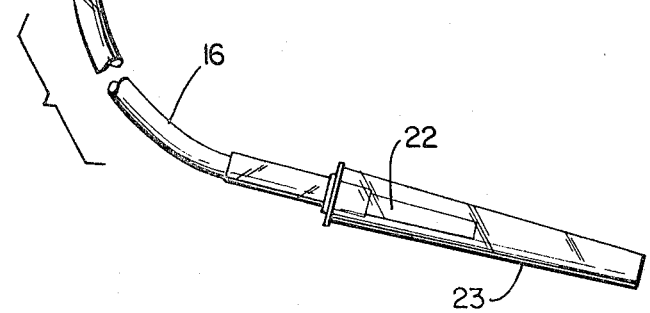

The present invention can best be understood by reference to the accompanying figures of drawings in which similar reference numerals are used for similar parts of the apparatus.

FIG. 1 depicts the unit package of the present invention which contains essential items for the diluent liquid vaccine supply system. Referring to FIG. 1, sterile diluent supply bottles 1 are supplied. These bottles contain the sterile diluent into which the vaccine, supplied separately, will be mixed in a manner to be subsequently described. These bottles may, for example, contain 60 ml. of sterile saline solution. The important factors here are that the diluent be sterile and that it be one which is a satisfactory diluent for the vaccine employed and also satisfactory for administration to the chicks. Such diluents are well known to the art-skilled.

The bottles are equipped with a tear-away outer aluminum seal and an inner aluminum cap which covers a rubber stopper which itself seals the bottle. The rubber stopper is adapted to be pierced by a transfer spike in connection with the transfer of the vaccine concentrate to the diluent supply bottles and subsequently, after transfer of vaccine concentrate is completed, the transfer spike is removed and the rubber stopper will receive the piercing piece of the drip chamber.

Also supplied is the transfer spike assembly 2. This assembly is shown in detail in FIG. 3. In this assembly, the transfer spike 3 is contained within a cover unit 4 which is sealed with a tear-away cover 5. This retains the transfer spike in sterile condition prior to its use. The end of the cover unit bearing the tear-away cover is adapted to receive the rubber stopper end of the diluent supply bottle in the manner shown in FIG. 5.

Figure 4:
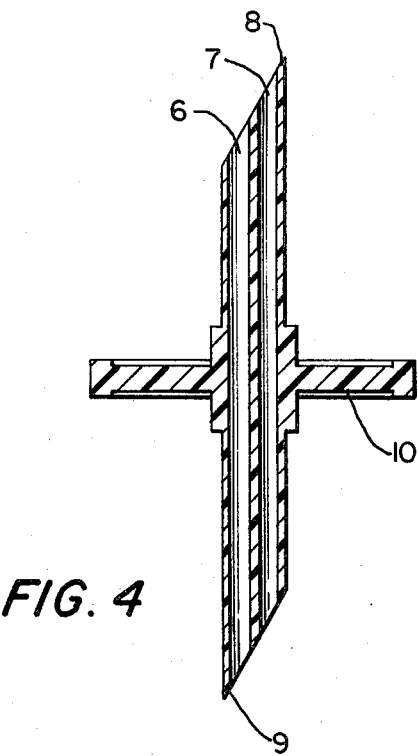
FIG. 4 is a sectional view of the transfer spike.

The transfer spike 3 itself (see FIG. 4) comprises parallel fluid passages 6 and 7 and flange 10. The fluid passages are of approximately equal length but are staggered so that the openings of the fluid passages on the bias-cut ends 8 and 9 are not immediately adjacent each other.

The ends 8 and 9 of the transfer spike are sufficiently sharp to easily pierce the rubber stoppers provided on both the diluent supply bottles 1 and the vaccine concentrate bottles to be described later.

Figure 5:
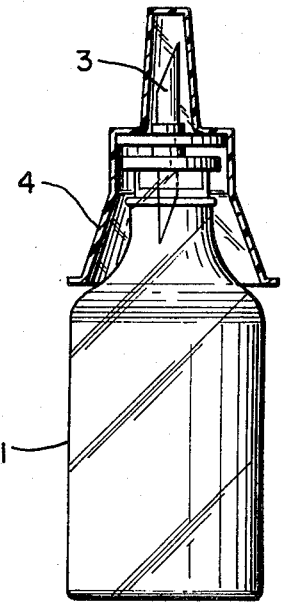
FIG. 5 is a partially sectional view of the transfer spike assembly and a sterile diluent supply bottle.

When the bias-cut end 8 of the transfer spike is inserted through the rubber stopper of the diluent supply bottle 1 as shown in FIG. 5, the flange 10 fits firmly against the rubber stopper and forms a fluid tight seal to prevent spillage during the transfer of the vaccine concentrate of the diluent supply bottle.

Also supplied as a part of the diluent liquid vaccine supply system is drip chamber-tubing-clamp assembly 11. This assembly is provided in sterile condition in a plastic envelope which is cut or torn to remove the contents. The assembly is supplied with a small piece of rubber tubing 12 which can be employed as an adaptor for connecting the tubing of the drip chamber-tubing-clamp assembly to the basic debeaking and vaccinating apparatus.

The drip chamber-tubing-clamp assembly is shown in more detail in FIG. 6. The drip chamber unit 13 is made up of a piercing spike 14 which is adapted for piercing the rubber stopper of the diluent supply bottle 1 after the vaccine concentrate has been transferred thereto and the transfer spike has been removed. This is best seen in FIG. 2.

The piercing spike 14 contains two bores or passages. One of these leads into the chamber 15 and conveys the liquid vaccine from the supply bottle 1 through tubing 16 to the basic debeaking and vaccination apparatus.

The other bore or passage through the piercing spike is for admitting relief air to the bottle as liquid is removed. This air passage contains a ball checkvalve which admits air to the bottle but prevents fluid flow from the bottle. A cap covers the end of the passage and contains a filter to prevent entry of bacteria and the like into the bottle.

The flange 18 provides the operator with means for grasping the drip chamber with the hand.

At a point below the drip chamber along tubing 16 there is present a clamp 19 for opening and closing the supply of liquid vaccine through the unit. This clamp can be any of the known types. Illustrated is the type containing a thumb operated roller 20 which is mounted so that when rotated downwardly it applies greater pressure on the tubing so as to ultimately close off entirely the flow of liquid therethrough.

The piercing spike 14 is covered by a cap 21 which is retained over the spike until the unit is ready for use at which time it is removed and discarded.

The end of tubing 16 is provided with a connector 22 which, either alone or with the rubber tubing adaptor 12, is used to connect the unit to the bassic debeaking and vaccination apparatus. The connector 22 is also covered with a cap 23 which is removed upon use and discarded.

In using the system of the present invention, the bracket 24 (see FIG. 2) which is supplied separately is attached to the basic debeaking and vaccination apparatus 25 (see FIG. 2). Such basic apparatus is known in the art as has been described previously and is thus not depicted in detail herein.

Figure 7:
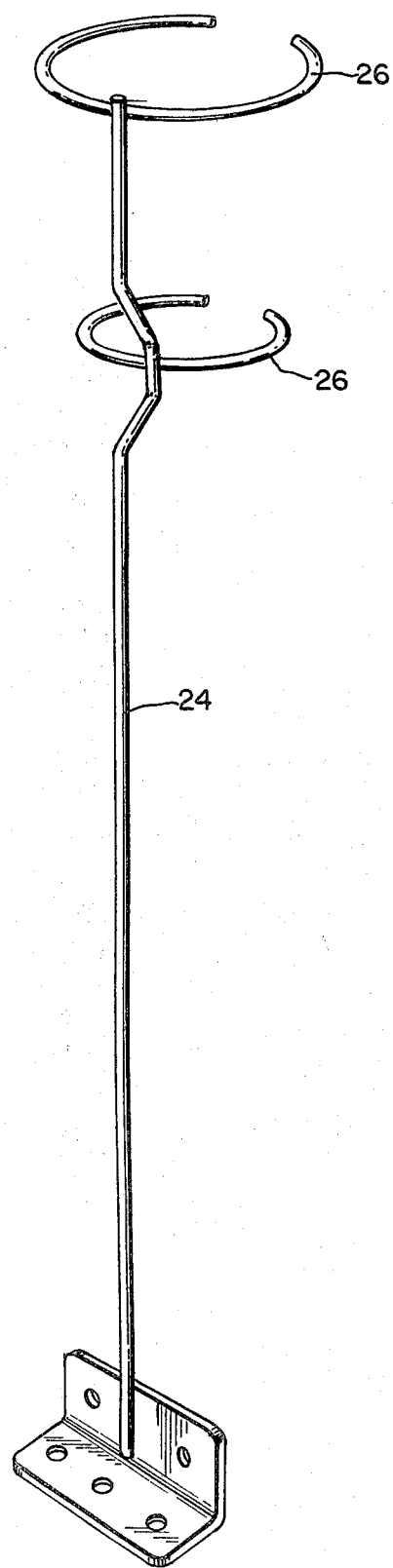
FIG. 7 is a perspective view of the bracket of the present invention.

The attachment is such that the liquid supply bottle 1 which is held by the bracket is located above the apparatus so that the liquid vaccine composition flows by gravity to the liquid injecting means portion of the apparatus. The bracket is shown in detail in FIG. 7.

The bracket, which may for example, be formed from metal, contains holding elements 26 which are adapted to receive the supply bottles 1 and hold them in place during delivery of the liquid vaccine composition.

Next it is necessary to rehydrate the vaccine which is supplied separately and generally in dehydrated form. The operator selects one of the liquid diluent supply bottles 1 and removes the outer aluminum seal and cap covering the rubber stopper. From the transfer spike assembly 2, the tear-away cover 5 is removed to reveal the bias-cut end 8 of the transfer spike. The end 8 is used to pierce the rubber stopper of the diluent supply bottle with the flange 10 resting flush against the rubber stopper. See FIG. 5. The cover unit 4 is then removed to expose end 9 of the transfer spike. End 9 is then used to pierce the rubber stopper of a bottle containing the dehydrated vaccine. The vaccine bottles are of generally the same design as the liquid diluent supply bottles but may be of smaller volume. The rubber stopper of these vaccine bottles is exposed in the same manner as bottles 1, i.e., by removing the outer aluminum seal and cap.

The thus achieved unit is then inverted to allow the diluent from the supply bottle 1 to fill the vaccine bottle. The unit is then thoroughly shaken to rehydrate the vaccine. The unit is then returned to the upright position allowing the rehydrated vaccine to return to the liquid diluent supply bottle 1.

Depending upon the amount of diluent in the supply bottle, the amount of vaccine in the vaccine bottle and the desired concentration of vaccine composition to be supplied to the chicks, this described process can be repeated by removing the vaccine bottle from the spike and using the end 9 to pierce the rubber stopper of a second vaccine bottle. In this way the contents of the second vaccine bottle can be rehydrated and transferred to the diluent supply bottle. When the desired amount of vaccine has been combined with the proper amount of diluent, the contents in the supply bottle are shaken thoroughly. The cover 4 is then replaced over the end 9 of the transfer spike and the end 8 of the transfer spike is removed from the rubber stopper of the supply bottle now containing the liquid vaccine composition. The transfer spike assembly is stored for future use. Alternatively, the transfer spike assembly can immediately be used to prepare other bottles of liquid vaccine for use on other debeaking and vaccination apparatus or a sufficient amount of liquid vaccine for a given period, e.g., two hours, can be prepared at one time.

The supply bottle containing the liquid vaccine composition is now connected to the drip chamber-tubing-clamp assembly. First the clamp 19 is closed to prevent flow of the liquid vaccine through the tubing. The cap 21 is removed to expose the piercing spike 14. This spike is used to pierce the rubber stopper of the supply bottle containing the liquid vaccine. The contact between the outer periphery of the spike and the rubber is sufficient to form a liquid tight seal.

The supply bottle with the drip chamber-tubing-clamp assembly attached is then placed in the bracket 24 as shown in FIG. 2.

The drip chamber and tubing is then primed, after removing the cap 23 which covers the connector 22 on the end of tubing 16, by carefully releasing the clamp 19. When the system is primed the connector 22, either alone or in conjunction with rubber tubing adaptor 12, is connected to the liquid vaccine injecting means portion of the basic apparatus. The system is then freed of air bubbles and the basic apparatus is adjusted to deliver the proper dosage of liquid vaccine.

The system of the present invention thus provides a simple and uncomplicated means for supplying liquid vaccine to the debeaking and vaccination apparatus.

In general the component parts of the system of the present invention are designed to be disposable in nature. It is contemplated that they will be used for a given time period, e.g., one day, and then destroyed. Burning of the component parts and unused contents is recommended.

What is claimed is:

1. A unit package for use in connection with a system for supplying liquid vaccine composition to an apparatus for substantially simultaneously debeaking and vaccinating poultry chicks said package comprising a compartmentalized container the compartments of which contain
   (a) a plurality of liquid diluent supply bottles containing sterile diluent for rehydrating dehydrated vaccine,
   (b) a transfer spike assembly comprising a cover unit sealed with a tear-away cover and containing a transfer spike suitable for providing sterile flow means from a liquid diluent supply bottle to a bottle containing dehydrated vaccine, and
   (c) a drip chamber-tubing-clamp assembly suitable for sterile transfer of liquid vaccine from a liquid supply bottle to the liquid injecting means of an apparatus for substantially simultaneously debeaking and vaccinating poultry chicks.

* * * * *